United States Patent [19]
Asoyan et al.

[11] Patent Number: 5,659,129
[45] Date of Patent: Aug. 19, 1997

[54] DEVICE FOR EXCITATION OF OSCILLATIONS AND DETERMINATION OF PROPERTIES OF VARIOUS FLUID MEDIA

[75] Inventors: Karen Vartgesovich Asoyan, Moscow; Vladimir Nikolaevich Belonenko, Moskovskaya oblast; Boris Vasilievich Makeev, Moscow; Mikhail Alexeevich Morozov; Armen Paruirovich Sarvazyan, both of Moskovskaya oblast, all of Russian Federation

[73] Assignee: Vserossiisky Nauchno-Issledovatelsky Institut Prirodnykh Gazoy I Gazovykh, Moscow, Russian Federation

[21] Appl. No.: 373,248

[22] PCT Filed: Jul. 22, 1993

[86] PCT No.: PCT/RU93/00172

§ 371 Date: Feb. 22, 1995

§ 102(e) Date: Feb. 22, 1995

[87] PCT Pub. No.: WO94/01989

PCT Pub. Date: Feb. 3, 1994

[30] Foreign Application Priority Data

Jul. 22, 1992 [RU] Russian Federation ............... 5055790

[51] Int. Cl.[6] ...................................................... G01N 11/10
[52] U.S. Cl. ................................. 73/54.25; 73/54.41
[58] Field of Search ................................ 73/54.24, 54.25, 73/54.26, 54.27, 54.41

[56] References Cited

U.S. PATENT DOCUMENTS

| | | |
|---|---|---|
| 2,490,452 | 12/1949 | Mason ........................ 177/386 |
| 2,607,216 | 8/1952 | Mason ........................ 73/53 |
| 3,525,252 | 8/1970 | Kocatas ........................ 73/54 |
| 4,893,046 | 1/1990 | Honda ........................ 310/323 |
| 4,920,787 | 5/1990 | Dual et al. ........................ 73/54 |
| 4,947,076 | 8/1990 | Kumada ........................ 310/323 |
| 5,433,112 | 7/1995 | Piche et al. ........................ 73/54.41 X |

FOREIGN PATENT DOCUMENTS

| | | |
|---|---|---|
| 0297032 | 12/1988 | European Pat. Off. . |
| 2620226 | 3/1989 | France . |
| 61-7251 | 3/1986 | Japan . |
| 61-7252 | 3/1986 | Japan . |
| 61-7253 | 3/1986 | Japan . |
| 198040 | 6/1967 | Russian Federation . |
| 930075 | 5/1982 | Russian Federation . |
| 1684627A1 | 10/1991 | Russian Federation . |
| 1704025 | 1/1992 | Russian Federation . |

OTHER PUBLICATIONS

"Measurement of the viscosity of liquids using quartz resonators", *Izmeritelnaya tekhnika*, No. 8, 1970, pp. 78–81.

*Primary Examiner*—Hezron E. Williams
*Assistant Examiner*—Jay L. Politzer
*Attorney, Agent, or Firm*—Gary M. Nath; Nath & Associates

[57] ABSTRACT

The device comprises an oscillator with electrodes, which is mounted in a casing, means for oscillation excitation, for measuring, recording and processing of signals, and a computer, the attachment of the oscillator being effected by means of balls with electroconducting surface and the oscillator being mounted in a holder with the possibility of movement in relation to the balls. The oscillator may be executed in different variants, for example in the form of a cylinder, disk, rod, plate, ball, and it may be hollow and may contain a partition as well as elements increasing its useful surface. The device is provided with a high-pressure vessel and is also used under high pressures.

18 Claims, 8 Drawing Sheets

DEVICE FOR EXCITATION OF OSCILLATIONS AND DETERMINATION OF PROPERTIES OF VARIOUS FLUID MEDIA

This invention relates to the field of investigations and analytical study of materials and it may be advantageously used for determination of critical parameters and physico-chemical, in particular, viscoelastic properties of various fluid media in oil and gas extraction, petrochemical and chemical industries, biology, biochemistry, medicine, etc.

Known in the prior art is a device designed to determine the parameters of a fluid medium and to monitor their variations, which device comprises a rocker rotatably suspended to a twistable cord. The rocker is swingable by an electromagnetic drive and carries, on one of its arms, a photoelectric transducer responsive to angular displacements and, on its opposite arm, a braking element dipped into a fluid medium under study (Ref. French Patent No. 2,620,226; G 01 N 11/14; 1989). However, the prior-art device suffers from a number of limitations, viz. it has a sophisticated mechanical structure, it has a poor sensitivity, it cannot be used under pressures different from atmospheric pressure, it employs time-consuming measurement procedures.

Also known in the prior art is a device adapted to determine parameters of a fluid medium, which device comprises a base plate a piezoelectric drive secured to the base plate and connected via a dielectric element to a piezoelectric receiver having a filament with a ball dipped into a fluid medium to be studied, the medium being poured into a thermostat-equipped vassel (U.S. Pat. No. 4,799,378; Int. Cl. G 01 N 11/16; 1989). The latter device also has a number of disadvantages, since it has a complicated structural arrangement, it cannot be used at high pressures, it has a low quality factor.

Equally known in the art is a device for determination of parameters of a fluid medium, which device comprises a hollow oscillator rigidly secured to a cantilever, a drive adapted to cause the oscillator to vibrate simultaneously at different vibratory modes, and vibration detection means, the drive and the detection means being formed as piesoelectric elements (Ref. Japanese accepted Application No. 67-7251; Int. Cl.G 01 N 9/00; 1986). The above-cited device has limited possibilities and is used mainly for density measurements. Besides, its sensitivity is rather low.

Also known in the art is a device adapted to determine parameters of a fluid medium, which device comprises a hollow pipe dipped into a medium under study, a piezoelectric drive rigidly attached to the hollow pipe, and a sensitive element (Ref. EP Application No. 0,297,032; Int. Cl.G 01 N 11/16; 1988). The art-known device also suffers from a great time lag, a poor accuracy and a low sensitivity.

The present invention makes departure from a device taken as prototype and described in the IZMERITEL'NAYA TEKHNIKA J. (Measuring Equipment), No.8, 1970, pp.78–81. The prototype device is intended to determine properties of various fluid media and comprises a casing provided with current lead-outs, an oscillator secured to a holder, fastening elements, means for pressing the fastening elements to the oscillator, surface electrodes connected to the current lead-outs, a unit for excitation of oscillations, and a unit for recording and processing signals. In the prototype device, the fastening elements of the oscillator are made in the form of filaments or knives pressed by flat springs against the lateral surface of the oscillator, or in the form of needles pressed against its axial ends. When needle-like fasteners are used, there arises friction between the oscillator surfaces and the needles, whereas when knife-like or filament-like fasteners are used, there takes place an inaccurate displacement of a line corresponding to zero mechanical vibrations and also displacement of a knife blade or filament holding the oscillator. The prototype device suffer from a number of limitations inherent in it: in the first place, it is difficult to adapt the process of its assembly and tuning to commercial-scale flow-line production conditions, since the non-perpendicularity of knives or non-coaxiality of needles to the oscillator surface are inevitable, while mechanical damage done to the oscillator by non-uniformly pressed fastening elements deteriorates its parameters.

To be specific, the electromechanical parameters in the prototype oscillator are determined using a bridge circuit which comprises a frequency meter and an oscillograph, and it is exactly the necessity to incorporate these units that represents a disadvantage of the prototype device, since it limits the field of its application because of its being so cumbersome, of its need for energy supply from a city power network and of its limited accuracy of measurements, as the latter presuppose visual observation of the measurement results on the cathode-ray tube of the oscillagraph. Besides, the oscillator gets excited in the prototype device by a radiopulse generator in a shock-excited manner, i.e. not only at the basic frequency, but also at its harmonics, whereby the measurement accuracy is considerably affected and the interpretation of measurements results is impeded.

The combined effect of the above-described limitations results in a poor reproducibility of measurements readings and a poor quality factor and, as a result, in a sensitivity inadequate for precise mesurements and in a great error of measurements of the parameters and properties of liquid media and, ipso facto, in an impossibility to obtain more or less tangible results for gaseous media.

The present invention is aimed at solving the problem of ensuring high-precision measurements both in liquid and gaseous media by improving the quality factor of the oscillator, its sensitivity and the measurement reproducibility.

The above-formulated object is accomplished owing to the fact that in a device intended to excite oscillations and to determine the properties of various fluid media, comprising an oscillator accomodated within a casing provided with current lead-outs and rigidly attached to a holder, fastening elements, means for pressing the fastening elements to the oscillator, electrodes attached to the casing surface and connected to the current lead-outs, a unit adapted to axcite oscillations of the oscillator, and a unit for recording and processing signals, there are incorporated improvements in accordance with the present invention, namely: said oscillator fastening elements are made in the form of balls, while said fastener pressing means are made in the form of a washer, the balls being provided with an electroconductive surface and pressed by the washer against the electrodes.

In all the cases of using the present invention, the above-described totality of its essential distinctive features proves to be fairly sufficient, since the balls provide a friction-reducing point contact with the resonator surface and, at the same time, represent points, at which the electrodes are connected to the current lead-outs. These improvements make it possible to overcome the above-mentioned limitations of the prototype, i.e. to improve its quality factor (figure of merits), its measurements results stability, its sensitivity, thereby permitting ultimately to expand the range of media amenable to study by the device of the present invention.

In accordance with some of its embodiments of the present invention, the oscillator is made one-piece from a piezocrystal or is provided with separate oscillation transducers mounted on its lateral or axial-end faces, or built-in into the oscillator body. Alternatively, these transducers may be formed of individual piezoelectric elements. They may envelope the entire surface of the oscillator. As possible alternatives, the oscillator may be formed cylindrical (disc-shaped) or spherical, one-piece or hollow, hollow with an internal partition, optionally with a partition pierced with an opening. Equally possible is to impart to the oscillator any other shape, combined shapes included, depending on the requirements imposed by specific operational conditions such as, e.g. they may have the form of concentrators (Ref. "ULTRASOUND: SMALL-SIZE ENCYCLOPOEDIA", edited by I. P. Golyamina, Sovetskaya Encyclopeodia Publishers, Moscow, 1979, p.171, p. 289).

A jumper (partition) may be also placed at the lines of zero mechanical oscillations. Whenever a jumper is there, balls may be placed in opposition to it. The ratio of the ball diameter to the diameter of the cylindrical oscillator may be comprised within from $1 \times 10^{-2}$ to $5 \times 10^{-1}$, while that of the ball diameter to the ocsillator length—within from $3 \times 10^{-3}$ to $3 \times 10^{-1}$. With smaller ratios difficulties arise in making fastenings, and with greater ratios the overall size of the device is unjustifiably increased. It is possible to excite oscillations of any type: torsional ones, longitudinal ones, etc., in a continuous mode, a pulsed mode, etc. Balls are pressed at points corresponding to oscillation nodes.

For the purpose of tuning, the oscillator is movable along balls. It is also possible to arrange balls and washers inside the oscillator. It is equally possible that the surfaces of balls and electrodes, with the exception of their contact areas, be isolated. Moreover, it is possible that to one of the axial ends of the device body an elastic, pressure-transmitting partition be attached to separate the medium under study from the outside.

The device of the present invention may also comprise a high-pressure vessel having electrodes connected to the current leadouts of the casing, and a sealing cover or covers with openings in which a dessicant or a filter are placed.

Said means for excitation of oscillations, for recording and processing of signals comprise a preamplifier-compensator adapted to receive a signal from a transducer, to amplify it and to correct direct passage of a noise signal, a phase shifter which is connected in series with the preamplifier-compensator and which comprises a built-in circuit for effecting jump-like phase shifts, thereby effecting corrections of phase distortions in the feedback loop circuit. The means in question further comprise an automatic amplification control system (AAC) intended to maintain constant a signal at the output of the preamplifier-compensator by varying the value of a signal at the imput of an integrator unit whose output signal serves as an input signal for the oscillator. Besides, the same integrator performs the function of an additional phase shifting device adapted to obtain an added-up phase shift equal to zero in the feedback loop circuit. To record signals, the device of the invention comprises a discriminator adapted to convert a signal issued from the output of the amplifier-compensator to a binary form, thus permitting to feed this signal into a measuring-and-controlling unit (MCU) intended to measure the signal frequency and to send a command to the phase shifter to carry out a jump-like phase shift in the feedback loop circuit. The measuring-and-controlling unit (MCU), in its turn, is integrated into a computer with an appropriate software, and sends its signals to the computer for their further processing.

The device of the present invention makes it possible to determine the resonant frequency (f) and the quality factor (Q), which may be conveniently represented by the value $\Delta \phi$, wherein $\Delta \phi = \Delta \phi c - \Delta \phi o$, $\Delta \phi c$ being the difference between a resonant frequency and the frequency of self-excited oscillations at a fixed phase shift in a medium under study, and $\Delta \phi o$ being the same in vacuum. The value $\Delta \phi o$ is related to the quality factor of the oscillator by the following equation:

$$Q = \frac{f}{2\Delta\phi}.$$

Figure 1:
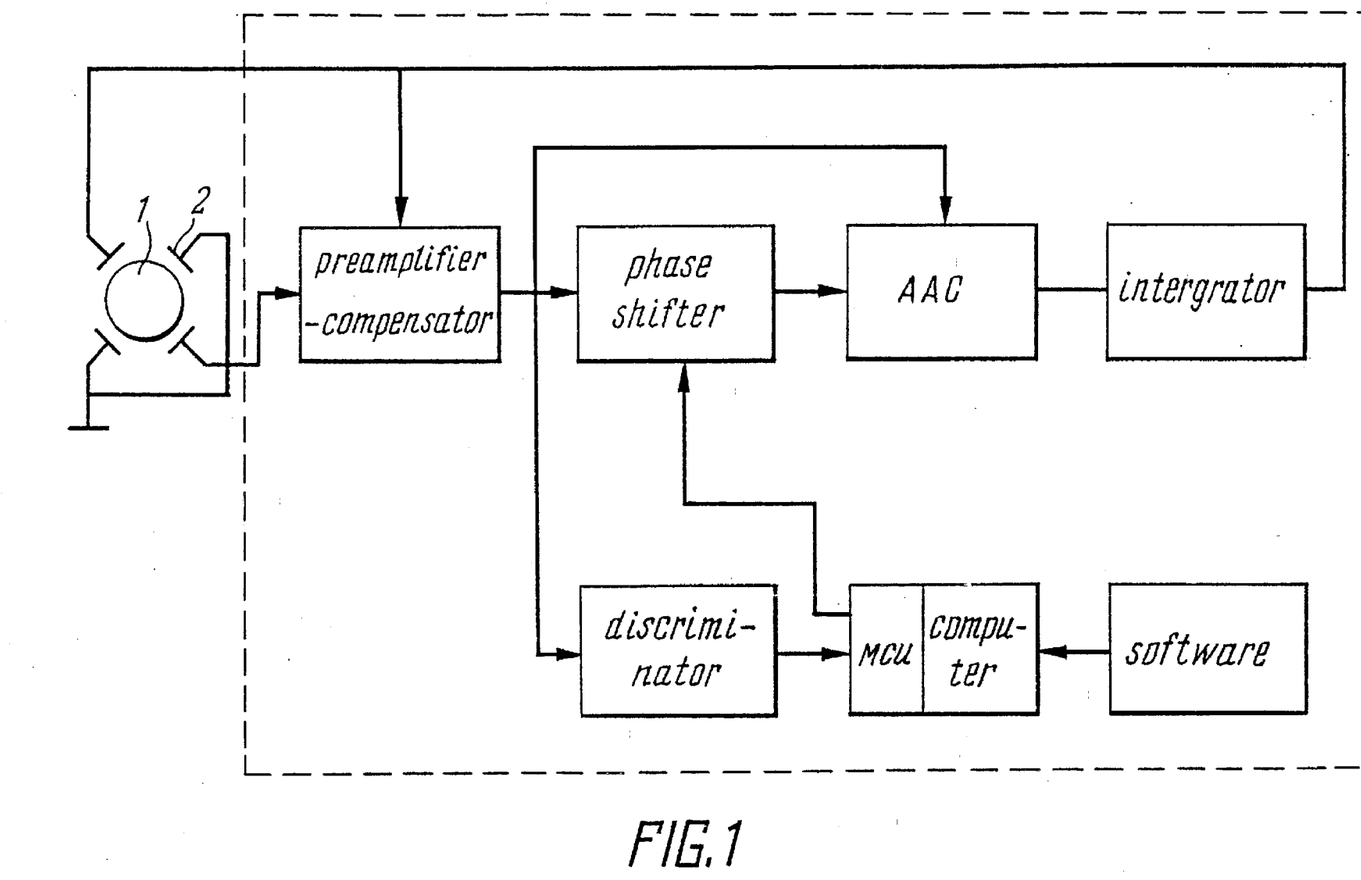
FIG. 1 represents the schematic diagram of means for excitation of oscillations, measuring and recording of signals.
Figure 2:
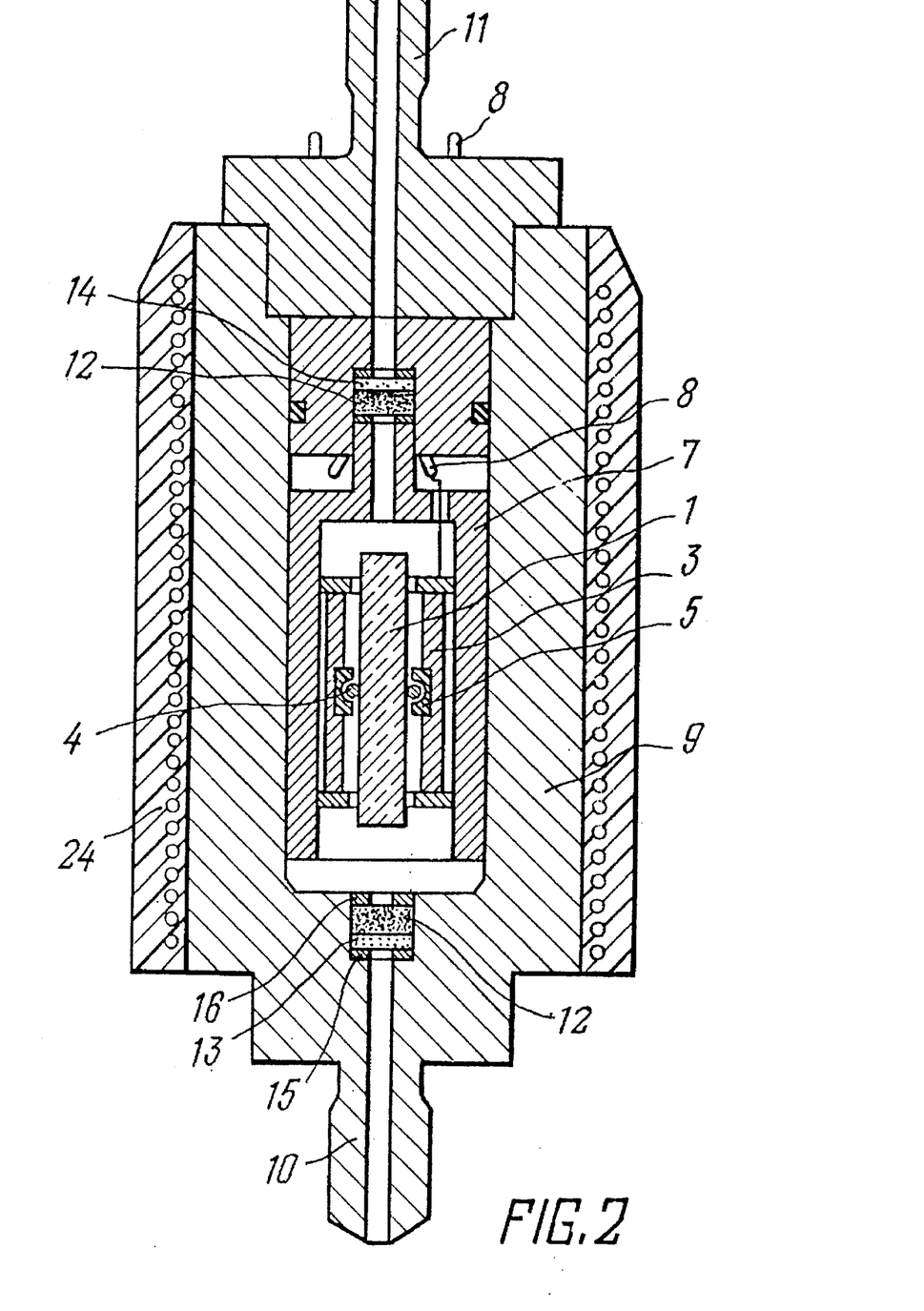
FIG. 2 schematically represents the layout of an oscillator in a high-pressure vessel.
Figure 3:
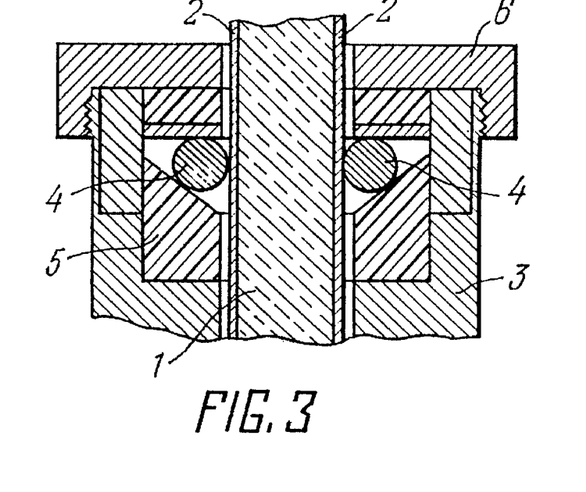
FIG. 3 represents an alternative embodiment for realization of fastening means for fixation of the oscillator.
Figure 4:
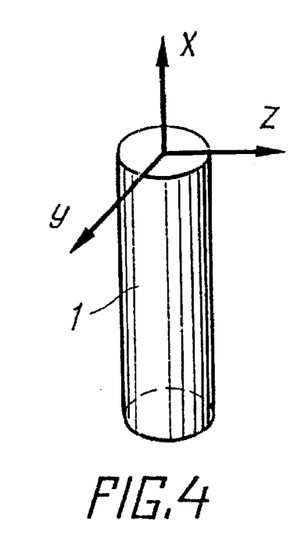
FIGS. 4 through 12 show different possible embodiments of oscillators.
Figure 5:
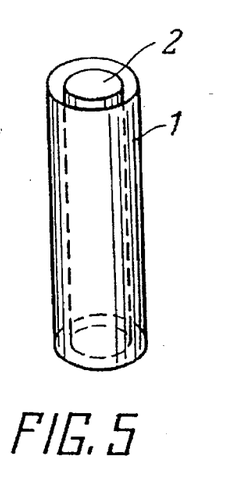

Now referring to FIG. 1, the device of the present invention comprises an oscillator 1 made, e.g. of a piezoelectric quartz crystal, in an X-cut, in the form of a cylinder provided with electrodes 2 applied thereonto by vacuum sputtering. The oscillator 1 is arranged with a play in a holder 3 with the help of a dielectric washer 5 adapted to press in place balls 4, a coupling nut 6 and the electrodes 2. The holder 3 is rigidly accomodated within a casing 7. The electroconductive surfaces of the balls 4 are connected via electrical contacts to the current lead-ins 7 of a hermetically sealed thick-walled thermostat-equipped high-pressure vessel 9 provided with connection inlet/outlet pipes 10 and 11 and with composite filters 12. The latter consist of a transverse layer of a porous material, a dessicant 13, and a porous membrane 14 arranged across or coaxially to the openings of the connection pipes 10 and 11. The entire assembly is braced by bracing elements 15 and 16.

Figure 6:
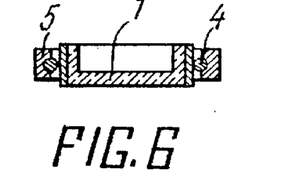
Figure 7:
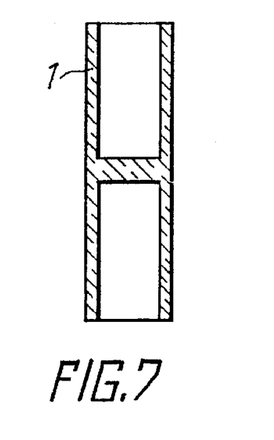
Figure 10:
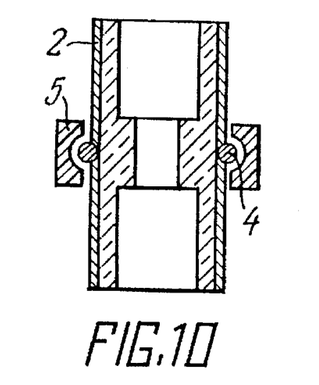
Figure 11:
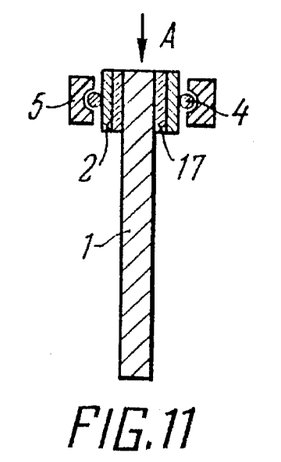
Figure 12:
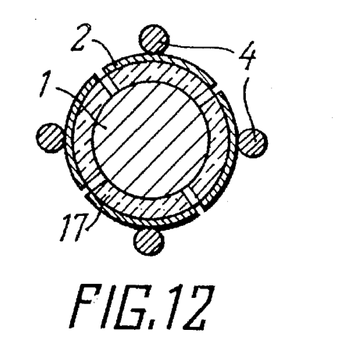
Figure 13:
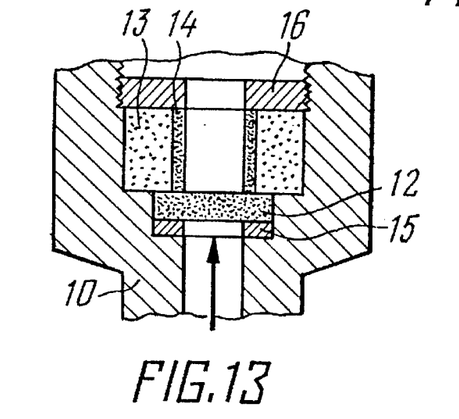
FIG. 13 represents an assembly for feeding a medium under study into the device of the invention.

The oscillator 1 may be also formed hollow as shown in FIGS. 5 to 8 and 10 in order to increase its contact surface area with a medium under study, or the oscillator 1 may be provided with a jumper (a blind one or one pierced with openings) as shown in FIGS. 6, 7 and 10, whereby a medium under study may be placed within the oscillator 1. The jumper (partition) is normally formed so as to be equal to a half-length of the oscillator 1 and to be placed in the middle of it (FIG. 7), whereby the hollow oscillator acquires the required rigidity, while its wall thickness is reduced.

Figure 8:
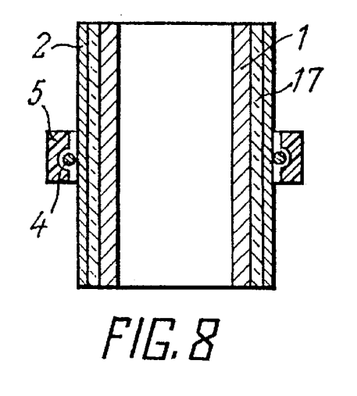
Figure 9:
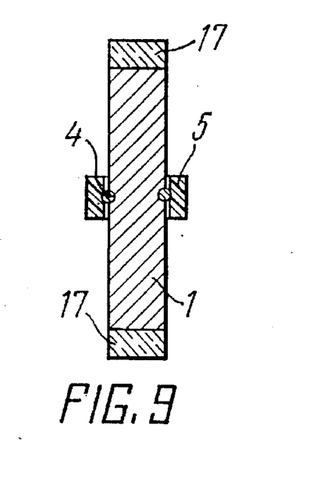

It is also possible to manufacture the oscillator from a material other than that specified above, in which case the piezoelectric elements 17 are attached to the oscillator 1 surface either as individual elements (FIG. 9), or as a continuous envelope (FIG. 8). These embodiments make it possible to vary the oscillatory modes over a wide range.

Figure 14:
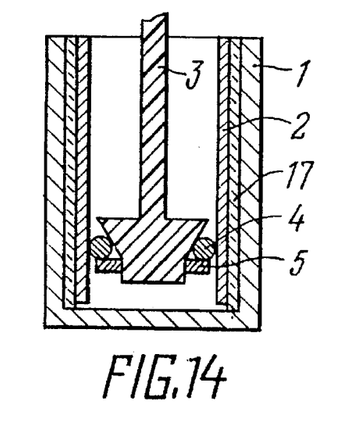
FIG. 14 schematically shows, how a holder is arranged inside an oscillator.
Figure 15:
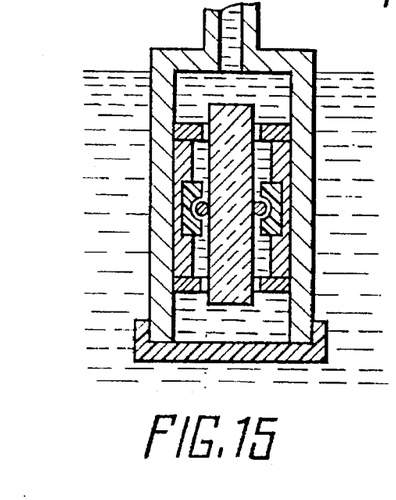
FIG. 15 schematically shows, how a medium under study is separated from outside.

Whenever a necessity arises to study electroconductive media, the balls and the electrodes, with the exception of their contact areas, are provided with an insulating monomolecular film made of silicone or some other dielectric material whose elastic properties cause low losses in the quality factor. In an embodiment in which the oscillator is made hollow, the holder 3 may be placed within the oscillator cavity (FIG. 14). The above-described embodiments of the oscillator 1 (FIGS. 4 through 11) provide favourable conditions for adequate use of the device of the present invention for investigating such or such medium under such or such specific conditions. Thus, for instance, in order to determine the bulk (volumetric) viscoelastic properties of a medium, it is preferable that a spherically shaped oscillator be used.

In order to achieve the desired properties of the device in question, it is necessary to aligh (adjust) the oscillator 1 in such a position as would ensure its greatest quality factor. To this effect, electric voltage is applied to the electrodes 2 and amplitude-frequency characteristics (AFC) and phase-frequency characteristics (PFC) are measured. Thereupon, gradual changes are effected in the spots of contact of the balls 4 with the electrodes 2 surface by axially displacing the oscillator 1 in the vicinity of the line of zero mechanical oscillations in the AFC and PFC modes so as to find the optimum mutual disposition of these elements corresponding to the maximum quality factor (figure of merit). Next, with the help of the washer 5, the balls 4 are pressed against the electrodes surface, thereby ensuring the optimum amplification of pressure in the AFC and PFC modes to correspond the peak values of the quality factor and measurement results stability in combination with an adequately rigid fastening system.

Figure 16:
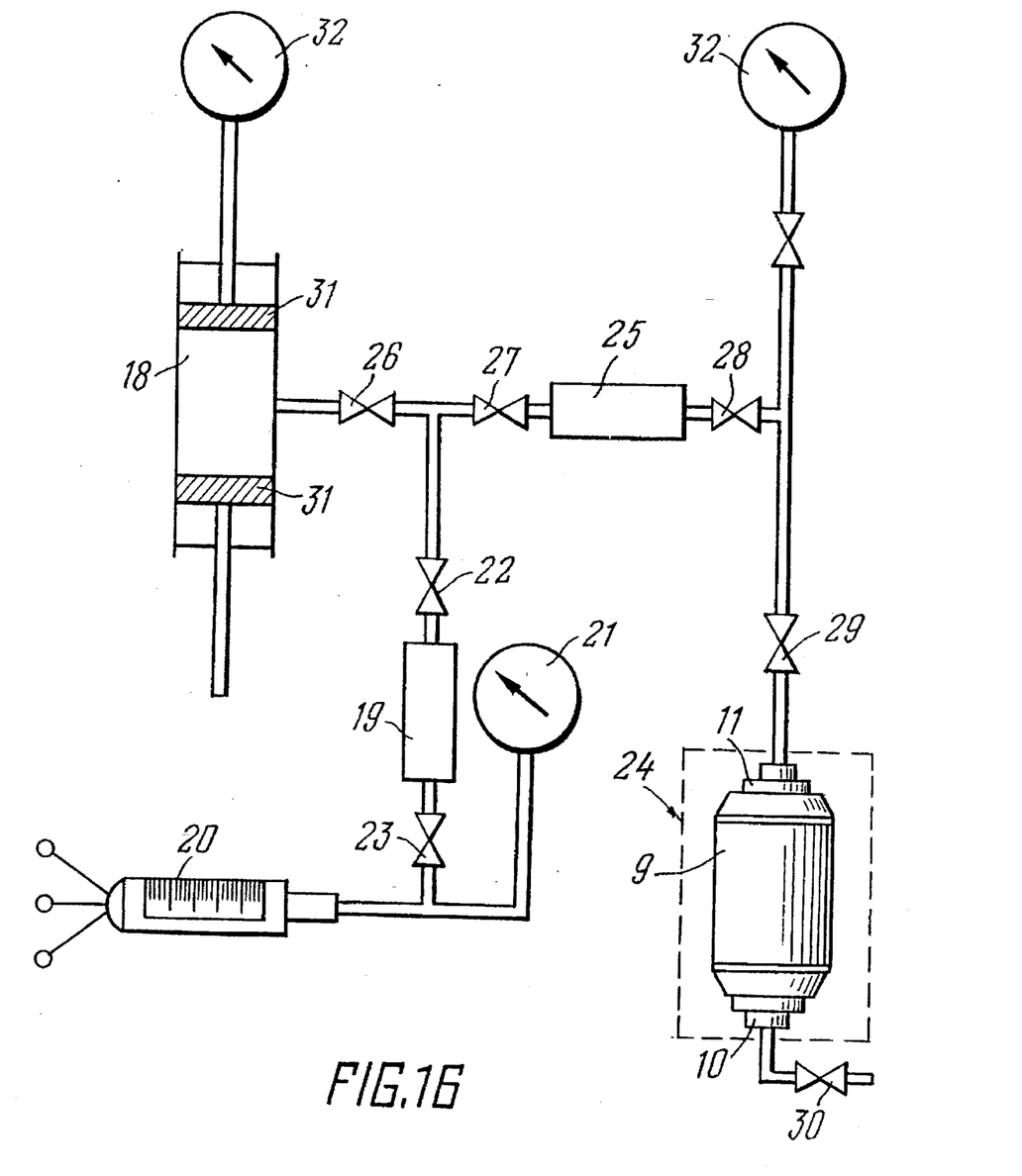
FIG. 16 schematically represents a stand for investigating hydrocarbon media.
Figure 17:
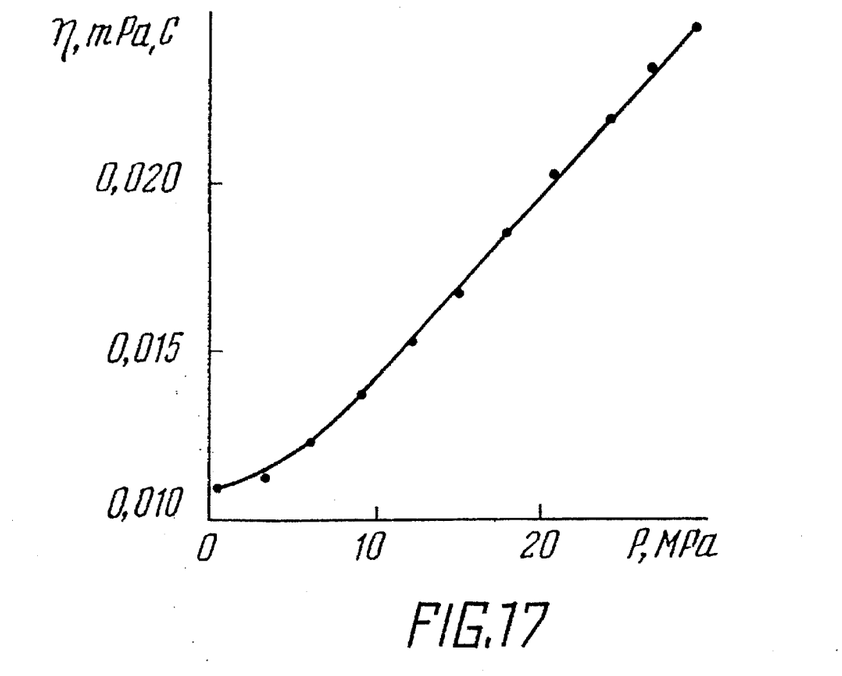
FIG. 17 represents a graph plotted on the results of a study of a viscosity versus pressure dependence in methane at a temperature of 20° C.
Figure 18:
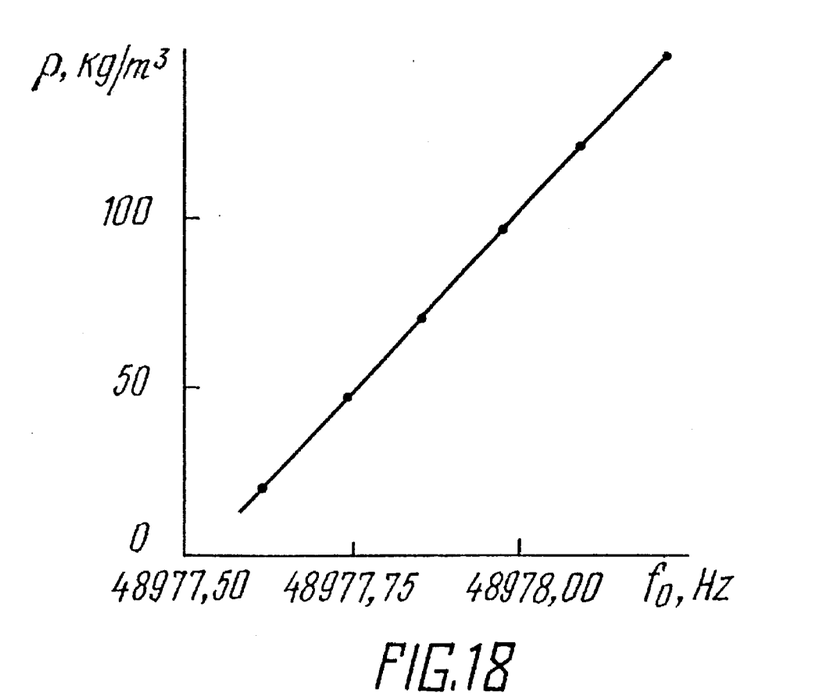
FIG. 18 represents a graph constructed to show a dependence of the oscillator's resonant frequency versus the density of a medium being studied.
Figure 19:
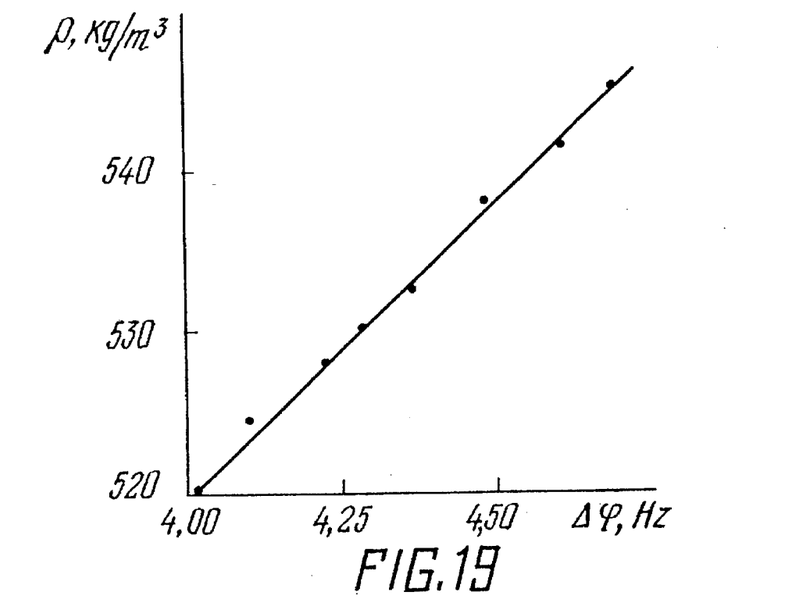
FIG. 19 represents a graphic dependence of the hydrocarbon's wide fraction density versus the value $\Delta \phi$.
Figure 20:
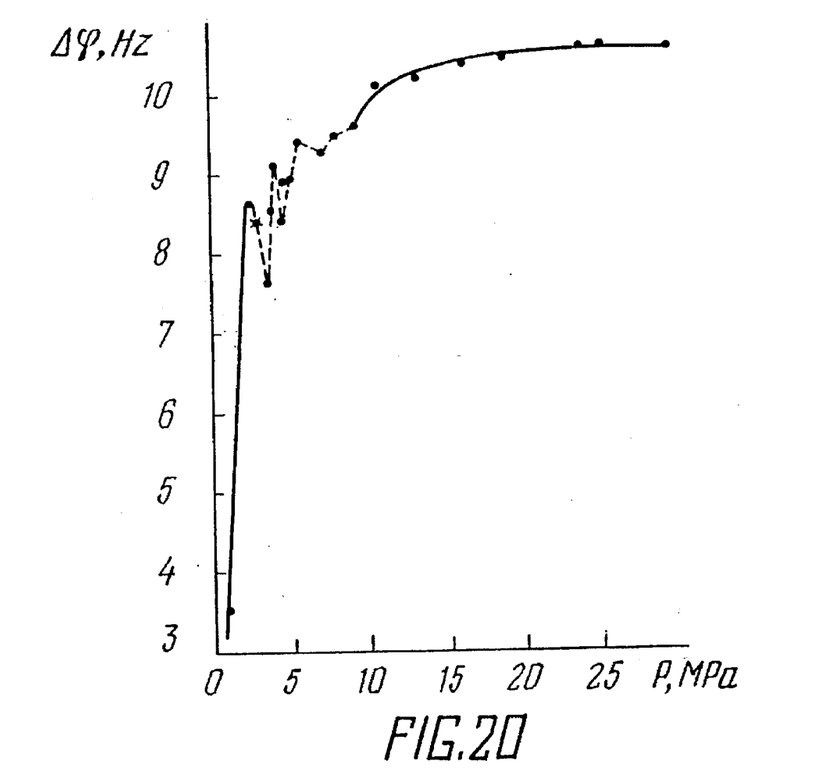
FIG. 20 represents a graph plotted to show $\Delta \phi$ versus pressure dependence for ethane at 20° C.
Figure 21:
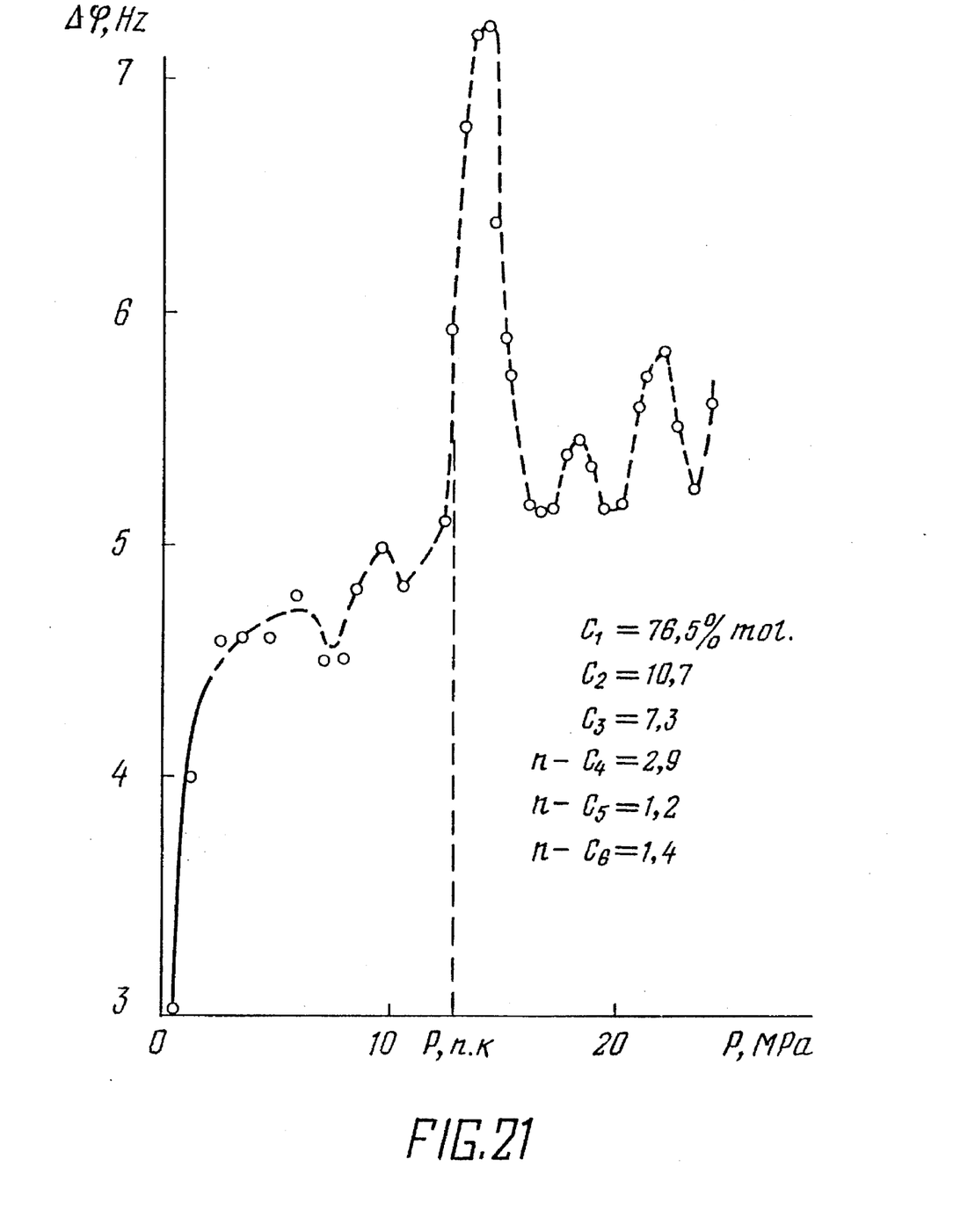
FIG. 21 represents $\Delta \phi$ variations as a function of pressure for a multi-component mixture at 20° C.

Various fluid media can be studied using the device in accordance with the present invention in, e.g. a test stand shown in FIG. 16, which stand comprises a vessel 18 adapted to prepare therein multi-component mixtures, detachable replaceable containers 19, a manually operated press 20, a pressure gauge 21, and valves 22 and 23. The high-pressure vessel 9 has a thermostatted jacket 24 and— via a filter 25 and valves 26, 27, 28 and 29—it is communicated with the vessel 18 and the container 19. A valve 30 is connected to the connection pipe 10 of the high-pressure vessel 9. The vessel 18 intended to prepare multi-component mixtures represents a thermostatted cylinder accomodating piston rods 31 actuated by diethylene glycol used as operating fluid. This cylinder also comprises pressure gauges 32 and viewing ports for visual observation of the phase condition of a multi-component mixture as an additional means of control (not shown in FIG. 16). The hand-operated press 20 is intended to provide a prescribed pressure in a container 19 enclosing a medium under study or a working fluid. The filter 25 is intended to ensure purification of a medium to be studied from water steam and other components dissolved therein, in particular, from diethylene glycol vapours. The medium thus made ready for study is admitted through the valve 29 into the high-pressure vessel 9 and the oscillator 1, while maintaining therein prescribed pressure and temperature at the required level.

Measurements are carried out in the following manner:

A medium under study is admitted into the vessel 9, and the resonant frequency of the oscillator 1 is measured, whereupon a phase jump signal is sent to the phase shifter (FIG. 1 ) and the frequency is measured of self-excited oscillations of the system with a fixed phase shift in the feedback loop circuit. Thereupon, a difference is measured between the resonant frequencies of self-excited oscillations at a fixed phase shift. This difference represents, in fact, the half-width of the transmission band of the oscillator. The difference is measured between the oscillator transmission half-widths in the medium under study and in vacuum. The magnitude of this difference make it possible to make judgement on the contribution made into the oscillator transmission band half-width of the medium under study. After calibration, the measured values make it possible to determine a good number of the properties of media being studied and to establish parameters of their condition, such as their viscosity, density, relaxation laxation time, constitutional composition, gas phase content in liquid, viscoelastic properties of liquids and elastic surfaces, etc. It is also possible to determine pressure and temperature of media under study. The device of the present invention also makes it possible to carry out measurements both in gases and in liquids, to investigate phase transitions, condensation and evaporation processes, to determine the dew point. As distinct from its prototype the device of the present invention offers a broader range of potentialities and applications. To be specific, the prototype device was unable to effect measurements in gases, to investigate fine physical processes and critical phenomena.

The potentialities of the present device and the range of properties that can be measured by it are considerably expanded, if use is made of two and more oscillators secured to holders with the aid of balls and connected, e.g. via a switchboard (commutator) to a unit for excitation of oscillations, for measuring, recording and processing signals according to the circuit shown in FIG. 1. What is more, incorporation of two or more oscillators improves accuracy and sensitivity of the device.

The fact that the balls have a point contact with electrodes, as well as the fact that electric voltage is applied to the oscillator and removed therefrom at the same spot at which the same oscillator is fixed in place, make it possible to considerably improve the quality factor (figure of merit) of the device and to stabilize the readings, i.e. to react to any changes in a medium under study at an earlier stage of their appearance.

The graphs shown in FIGS. 17–21 illustrate the level attainable by the device of the present invention. The use of a point contact, while improving the sensitivity of the device, makes it possible to reduce the oscillator diameter, whereas the presence of an electroconductive material on the ball surface offers the advantage of combining the function of a holder with that of electric voltage supply, i.e. to minimize the number of structural elements making part of the device, improving ipso facto the stability, dependability and accuracy of its functioning. Furthermore, the function of a holder is combined not only with the function of voltage supply, but also with the function of reduced friction in the assembly of fixation of the oscillator, whereby the range of potentialities of the device is significantly expanded, which is particularly important during measurements in weakly viscous media.

Consequently, the device of the present invention features a high sensitivity, accuracy, stability and reliability of measurements, simplicity of adjustment and amenability to commercialscale on-stream production. The above-enumerated advantages permit to employ the device for effecting measurements of the thermodynamic, physico-chemical, rheological, mechanical, etc. properties of various media over a wide range of fluctuations of their parameters; to study critical phenomena concentration dependences, etc.

What is claimed is:

1. A device for excitation of oscillations and determination of properties of various fluid media, comprising:

a hermetically sealed, thick walled, thermostat-equipped high pressure vessel;

an oscillator accommodated in a casing having current lead-outs all located within said high pressure vessel;

electrodes arranged on the casing surface and connected to the current lead-outs;

a holder adapted to fix in place the oscillator including fastening and pressing elements wherein said fastening and pressing elements are made in the form of balls having electroconductive surfaces and further including washer means for pressing said balls against said electrodes;

means for excitation of oscillator oscillations; and means for measuring, recording and processing of signals for determining visco-elastic properties;

wherein said means for excitation of oscillations and said means for measuring, recording and processing of signals comprise:

a preamplifier-compensator having one of its inputs connected to the oscillator output and having its other input connected to the oscillator input;

a phase shifter having one input connected to an output of the preamplifier-compensator, while its other input is connected to the output of a measuring-and-controlling input;

an automatic amplification control system having one input connected to the phase shifter output, while its other input is connected to the preamplifier-compensator output;

an integrator whose input is connected to the output of said automatic amplification control system, while its output is connected to the oscillator input;

a discriminator with an input connected to said preamplifier-compensator output, while its output is connected to the input of said measuring-and-controlling unit having its output connected to a computer.

2. A device as claimed in claim 1, characterized in that its oscillator is formed of a piezocrystal.

3. A device as claimed in claim 1, characterized in that said oscillator is provided with one or more oscillations transducer(s) arranged on its surface.

4. A device as claimed in claim 3, characterized in that said oscillations transducers are disposed at the axial ends of the oscillator, while said balls are pressed against the oscillator body at the nodal points of oscillations.

5. A device as claimed in claim 1, characterized in that said oscillator is provided with an oscillations transducer extending all over its surface.

6. A device as claimed in claim 4, characterized in that said oscillations transducers are made of piezoelectric elements.

7. A device as claimed in claim 1, characterized in that said oscillator is made cylindrically shaped.

8. A device as claimed in claim 1, characterized in that said oscillator is made spherically shaped.

9. A device as claimed in claim 1, characterized in that said oscillator is made hollow.

10. A device as claimed in claim 1, characterized in that said oscillator is formed with an internal jumper.

11. A device as claimed in claim 10, characterized in that said jumper is formed with an opening.

12. A device as claimed in claim 11, characterized in that said balls are disposed opposite said jumper.

13. A device as claimed in claim 1, characterized in that, with the exception of contact areas, the surfaces of the balls and electrodes are electrically insulated.

14. A device as claimed in claim 8, characterized in that the ratio of the ball diameter to the oscillator diameter ranges from $1 \times 10^{-2}$ to $5 \times 10^{-1}$.

15. A device as claimed in claim 1, characterized in that said oscillator is arranged so as to be movable relative to said balls.

16. A device as claimed in claim 1, characterized in that said fastening and pressing elements are disposed within said oscillator.

17. A device as claimed in claim 1, characterized in that it is provided with an elastic membrane or partition arranged at one of the axial ends of the casing for isolating a medium under study from an outside medium.

18. A device as claimed in claim 1, characterized in that it comprises a high-pressure vessel provided with current inputs connected to the current lead-outs of the casing, and also comprises a sealed lid having an opening in which a dessicant and/or a filter are placed.

* * * * *